(12) United States Patent
Schuler et al.

(10) Patent No.: US 11,129,627 B2
(45) Date of Patent: Sep. 28, 2021

(54) METHOD AND APPARATUS FOR INSERTING A BONE PLATE

(71) Applicant: GLOBUS MEDICAL, INC., Audubon, PA (US)

(72) Inventors: Olivia Schuler, Levittown, PA (US); Gabrielle Zingalis, Philadelphia, PA (US); Evan Langdale, Philadelphia, PA (US); Peter Evans, Lafayette Hill, PA (US)

(73) Assignee: Globus Medical, Inc., Audubon, PA (US)

( * ) Notice: Subject to any disclaimer, the term of this patent is extended or adjusted under 35 U.S.C. 154(b) by 26 days.

(21) Appl. No.: 16/668,824

(22) Filed: Oct. 30, 2019

(65) Prior Publication Data

US 2021/0128176 A1    May 6, 2021

(51) Int. Cl.
| | |
|---|---|
| *A61B 17/17* | (2006.01) |
| *A61B 17/16* | (2006.01) |
| *A61B 17/80* | (2006.01) |
| *A61B 17/84* | (2006.01) |

(52) U.S. Cl.
CPC .......... *A61B 17/17* (2013.01); *A61B 17/1637* (2013.01); *A61B 17/808* (2013.01); *A61B 17/8061* (2013.01); *A61B 17/84* (2013.01)

(58) Field of Classification Search
CPC ... A61B 17/7059; A61B 17/808; A61B 17/88; A61B 17/8872; A61B 2017/90
See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |
| 3,463,148 A | 8/1969 | Treace |
| 3,695,259 A | 10/1972 | Yost |
| 3,716,050 A | 2/1973 | Johnston |
| 4,187,840 A | 2/1980 | Watanabe |
| 4,219,015 A | 8/1980 | Steinemann |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Matthew J Lawson

(57) ABSTRACT

Devices, systems, and methods for locking a drill guide into a polyaxial hole while maintaining the form and function of the polyaxial hole are provided herein. In some embodiments, the drill guide includes a hollow outer body extending from a proximal end to a distal end and having a slot disposed proximate the proximate end, wherein the distal end is configured as a reverse collet having a plurality of prongs; an inner body having a central channel extending therethrough; and a lever coupled to the inner body through the slot, wherein the slot is shaped such that rotation of the lever results in motion along a central axis of the drill guide, and wherein a distal end of the inner body is configured to prevent radially inward deflection of the plurality of prongs when the inner body is in a lowermost position.

5 Claims, 11 Drawing Sheets

(56) References Cited

U.S. PATENT DOCUMENTS

| | | |
|---|---|---|
| 4,781,183 A | 11/1988 | Casey et al. |
| 4,867,144 A | 9/1989 | Karas et al. |
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,916,323 B2 * | 7/2005 | Kitchens ............ A61B 17/1725 606/104 |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,766,916 B2 * | 8/2010 | Leyden ............ A61B 17/1728 606/86 B |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,231,627 B2 | 7/2012 | Huebner et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |

(56) References Cited

U.S. PATENT DOCUMENTS

| | | |
|---|---|---|
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 9,814,504 B2 | 11/2017 | Ducharme et al. |
| 10,159,514 B2 | 12/2018 | Perrow et al. |
| 10,357,294 B2* | 7/2019 | Medoff .................. A61B 17/80 |
| 2002/0045901 A1 | 4/2002 | Wagner et al. |
| 2002/0147450 A1 | 10/2002 | LeHuec et al. |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0241607 A1 | 10/2006 | Myerson et al. |
| 2007/0173840 A1 | 7/2007 | Huebner |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0261674 A1* | 10/2013 | Fritzinger ............ A61B 17/808 606/286 |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0080975 A1 | 3/2015 | Pleil |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |

(56) References Cited

U.S. PATENT DOCUMENTS

| | | |
|---|---|---|
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0000534 A1 | 1/2017 | Medoff |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0151064 A1 | 6/2017 | Armstrong et al. |
| 2017/0215931 A1 | 8/2017 | Cremer et al. |
| 2019/0046251 A1 | 2/2019 | Detweiler et al. |
| 2019/0110821 A1 | 4/2019 | Perrow et al. |
| 2019/0314042 A1* | 10/2019 | Laird, Jr. ........... A61B 17/1728 |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| EP | 1661525 A2 | 2/2007 |
| EP | 3552562 A1 | 10/2019 |
| FR | 2846870 A1 | 5/2004 |
| FR | 2928259 A1 | 9/2009 |
| JP | 2003210478 A | 7/2003 |
| TW | 201316942 A | 5/2013 |
| WO | 2016079504 A1 | 5/2016 |

* cited by examiner

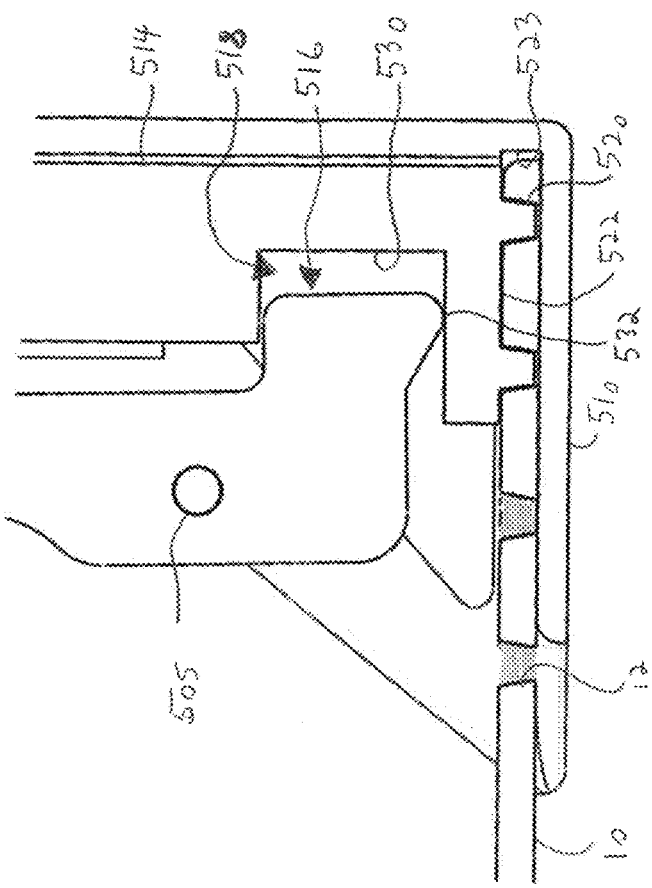
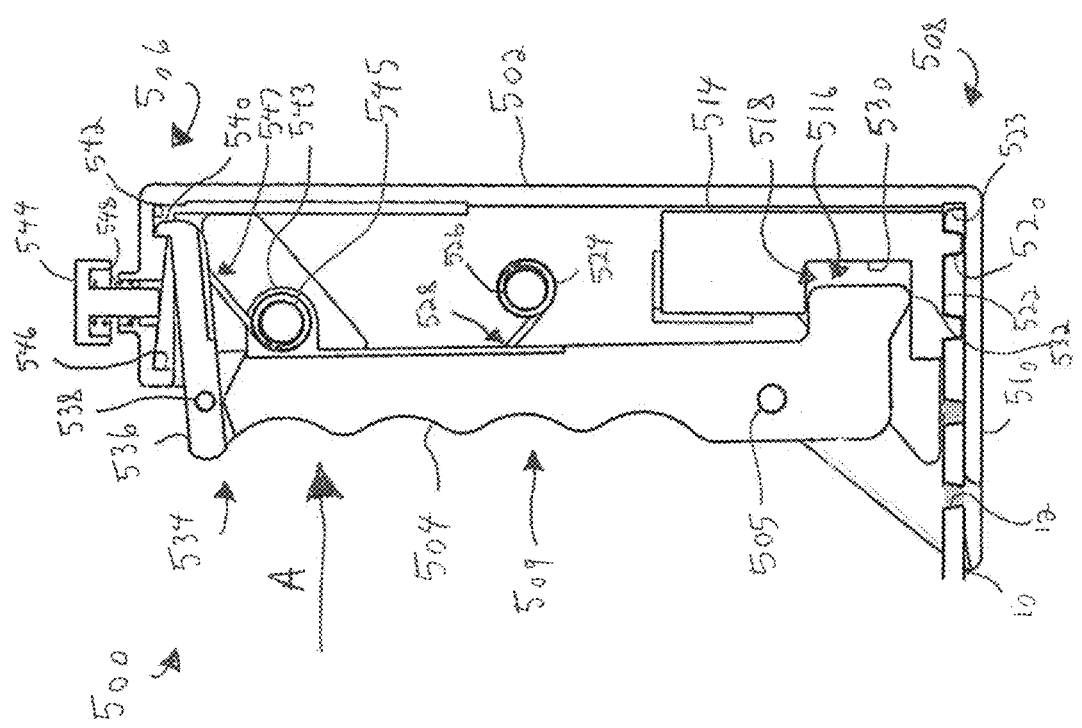
FIG. 5D
FIG. 5C

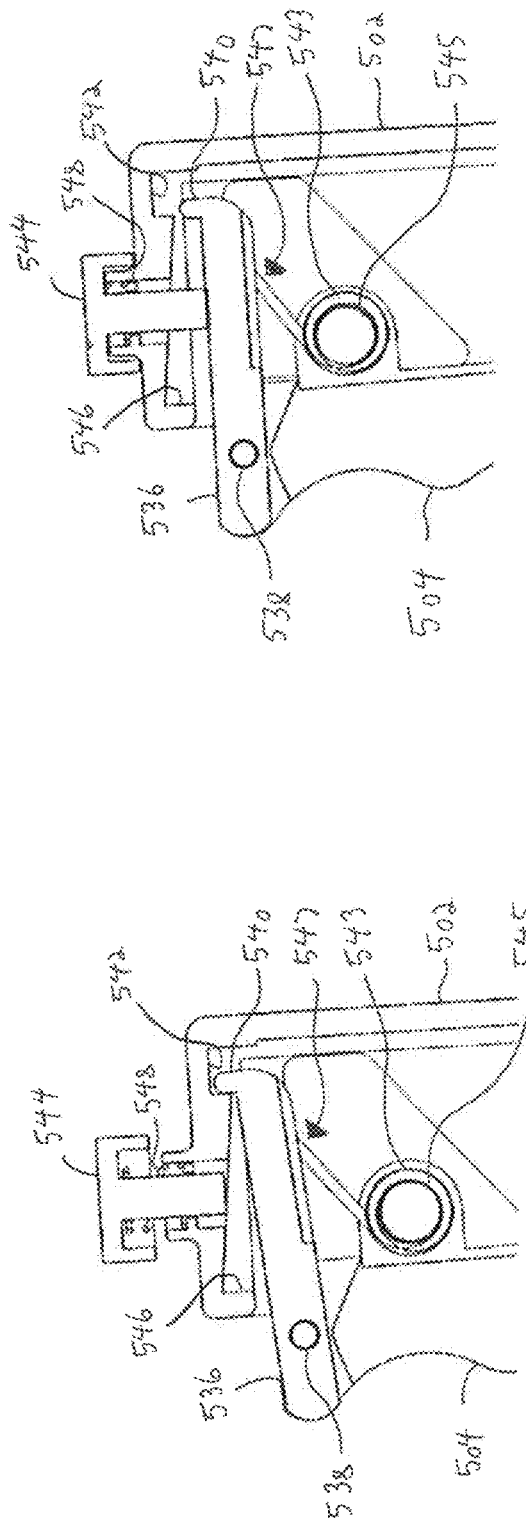
FIG. 5E
FIG. 5F
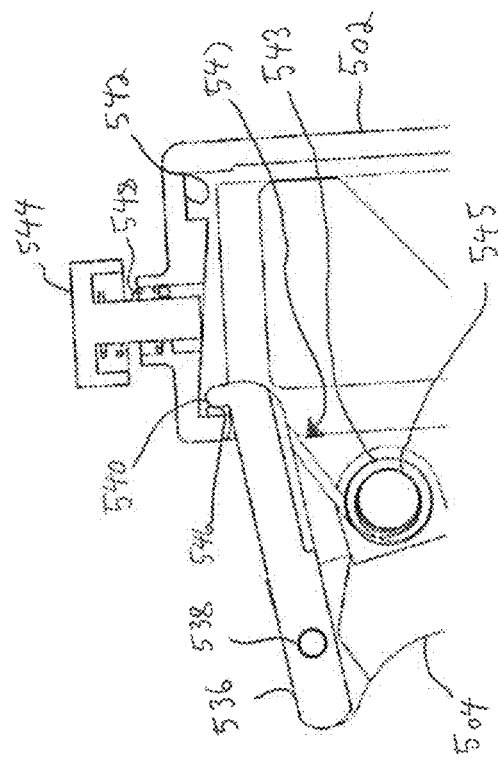
FIG. 5G

METHOD AND APPARATUS FOR INSERTING A BONE PLATE

FIELD

The present disclosure relates to surgical devices, and more particularly, stabilization systems, for example, for trauma applications.

BACKGROUND

Bone fractures are often repaired by internal fixation of the bone, such as diaphyseal bone, using one or more plates. The plate is held against the fractured bone with screws, for example, which engage the bone and heads, which provide a compressive force against the plate. The plate and bone are thus forced against each other in a manner that transfers load primarily between a bone-contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. Of course, the designs of the plates may vary based on the location and type of fracture.

Without a handle attachment or similar apparatus, it can be difficult to maintain a firm grip on a plate during insertion of the plate through an incision, accurately place the plate, or apply any force(s) required for manipulation of the plate in different areas of the patient's body.

SUMMARY

To meet this and other needs, devices, systems, and methods for inserting a plate are provided herein. In some embodiments, an apparatus for inserting a bone plate to a target site, the apparatus includes a body extending from an upper end to a lower end; a plate receiving portion configured to receive the bone plate; and a plate engaging mechanism configured to couple the bone plate to the body, wherein the body includes a gripping surface configured to be gripped by a user's hand.

BRIEF DESCRIPTION OF THE DRAWING

A more complete understanding of the present invention, and the attendant advantages and features thereof, will be more readily understood by reference to the following detailed description when considered in conjunction with the accompanying drawings wherein:

FIGS. 5A-5I depict an apparatus for inserting a plate in accordance with embodiments of the present disclosure.

DETAILED DESCRIPTION

Figure 1A:
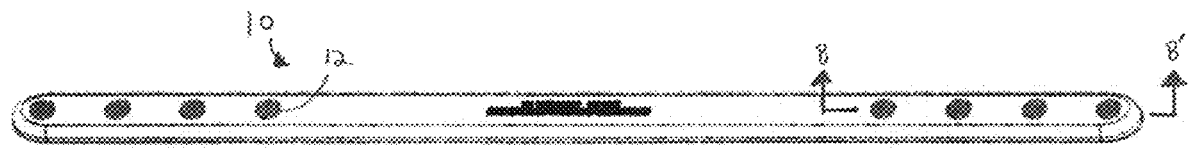
FIG. 1A depicts a trauma plate suitable for use with a plate inserter in accordance with embodiments of the present disclosure.

Embodiments of the disclosure are generally directed to devices, systems, and methods for inserting a plate through an incision and to a target area within a patient. Specifically, embodiments are directed to a plate inserter configured to advantageously allow for the plate to be coupled to the inserter on a back table or intra-operatively to an end of a plate opposite an end already fixed to bone. The inventive inserter also advantageously provides a low profile on the lowermost surface of the inserter (i.e., the portion that couples to the plate) to avoid soft tissue irritation, ease of operation with one hand, and a comfortable grip that fits the contours of a user's hand.

Although the following description and the figures show a specific plate, it should be noted that the inventive plate inserter may be used with any type of plate. Exemplary plates may include plates adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plate may be curved, contoured, straight, or flat. The plate may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Figure 1B:
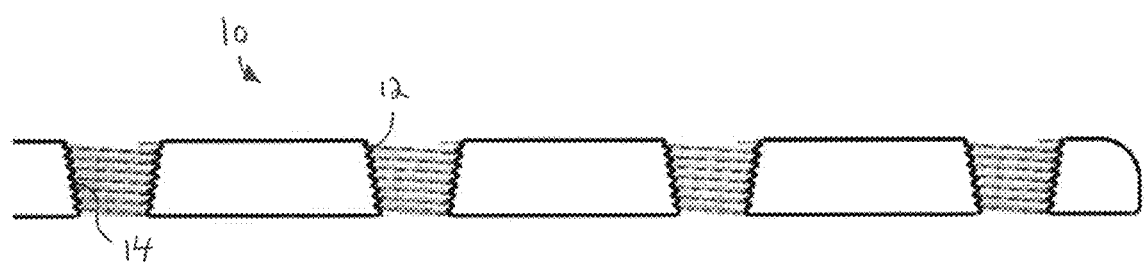
FIG. 1B is a cross-sectional view of the plate of FIG. 1A taken along line B-B'.

Referring now to the drawings, FIGS. 1A and 1B depict an elevated side view and a cross-sectional view, respectively, of a plate 10 including at least one opening such as, for example, a hole 12 (eight holes shown in FIG. 1A). The hole 12 extends through the plate 10 and is configured to accept a fastener (not shown) that is able to dynamically compress the bone and/or affix the plate 10 to the bone. As shown more clearly in FIG. 1B, the hole 12 may include threads 14 configured to correspond to threads of a fastener (not shown).

Figure 2:
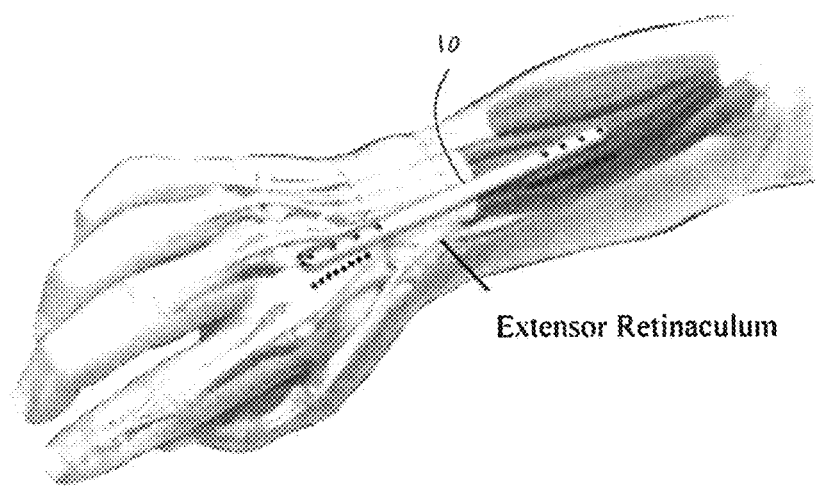
FIG. 2 depicts the trauma plate of FIGS. 1A and 1B implanted in a patient.
Figure 3:
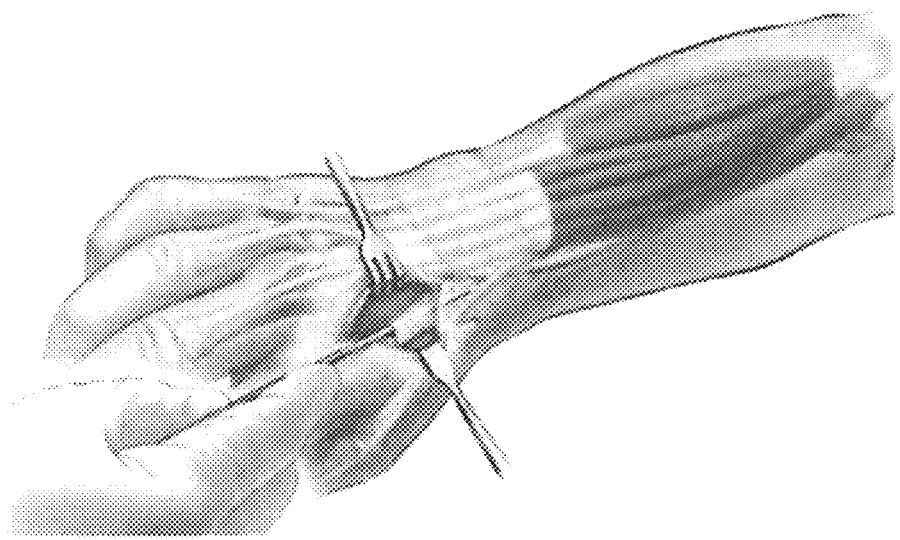
FIG. 3 depicts the retraction of patient anatomy to implant the trauma plate of FIGS. 1A and 1B.

FIG. 2 illustrate the plate 10 implanted along the dorsal side of a patient's hand. FIG. 3 depicts the retraction necessary to access the dorsal side of the patient's hand to implant the plate 10. The opening that permits access to the target site is extremely small. As such, it has been difficult to place and manipulate such a plate during the implantation process.

FIGS. 4A-4D depict a plate inserter 400 in accordance with embodiments of the present disclosure. In some embodiments, the plate insert 400 includes a body 402 extending from an upper end 404 to a lower end 406. The lower end 406 includes an opening 407 configured to receive a portion of the plate 10 to be held by the plate inserter 400. The body 402 further includes a gripping portion 408 configured to easily be gripped by a user's hand. A plate locking mechanism 410 is disposed within the body 402. In some embodiments, the plate locking mechanism 410 includes an actuator 412, which extends through the upper end 404. The actuator 412 includes a rotatable lever 414 coupled to an actuator body 416. The actuator body 416 includes a protruding element 418 that extends radially outward from the actuator body 416 into a groove 420 formed on an interior wall 422 of the body 402. The groove 420 is sloped such that when a user turns the lever 414 (and thus the actuator body 416) in a first direction (indicated by arrow A in FIG. 4B), movement of the protruding element 418 along the groove 420 forces the actuator body 416 to move downwards. Turning the lever 414 in a second direction (indicated by arrow B in FIG. 4C) opposite the first direction forces the actuator body 416 to move upwards.

Figure 4A:
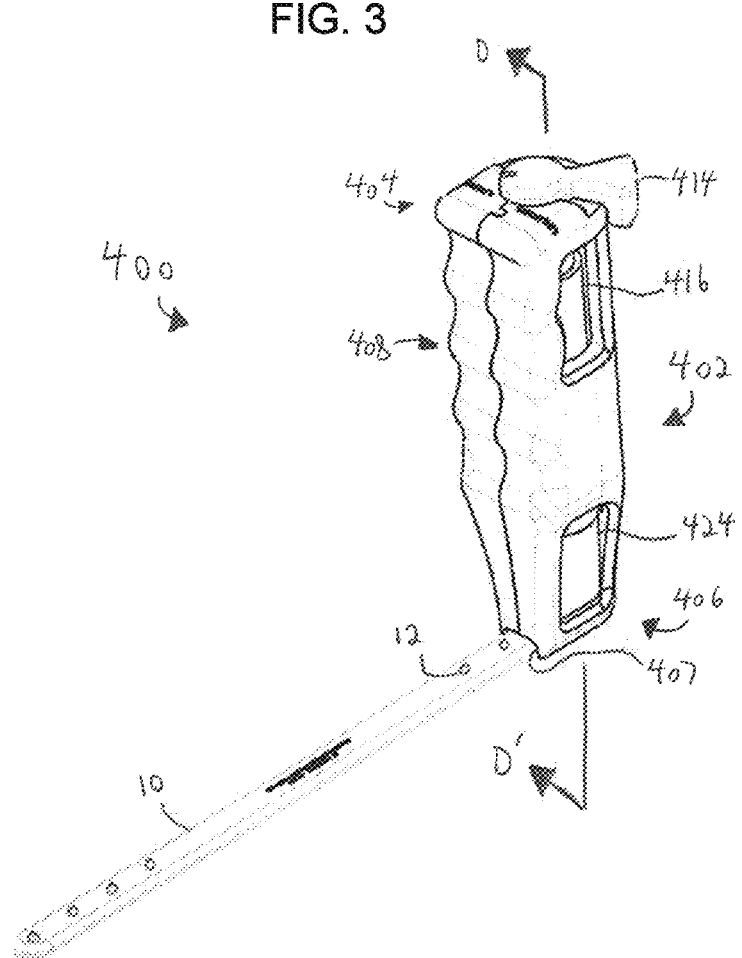
FIGS. 4A-4D depict an apparatus for inserting a plate in accordance with embodiments of the present disclosure.
Figure 4B:
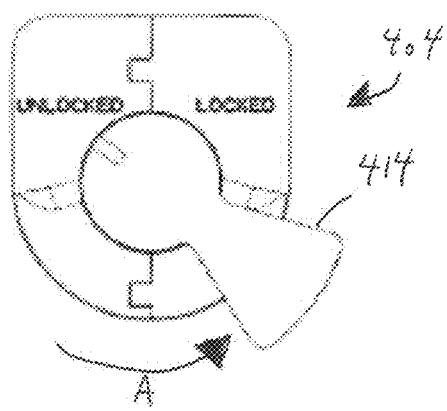
Figure 4C:
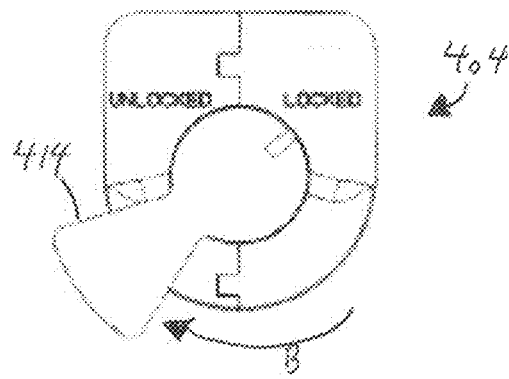
Figure 4D:
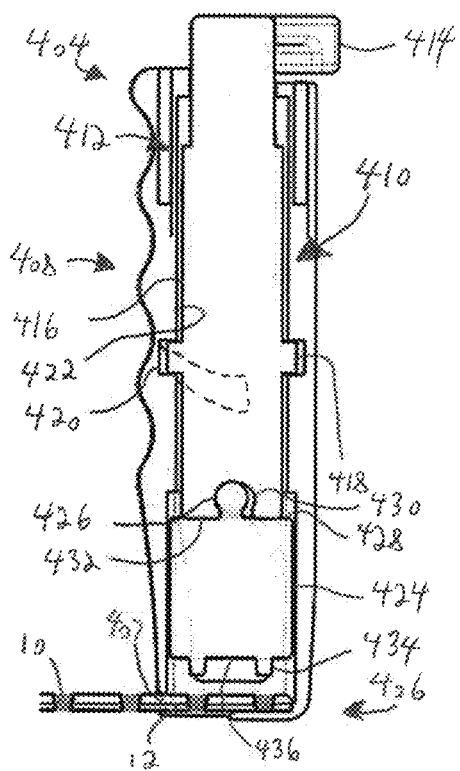
Figure 5A:
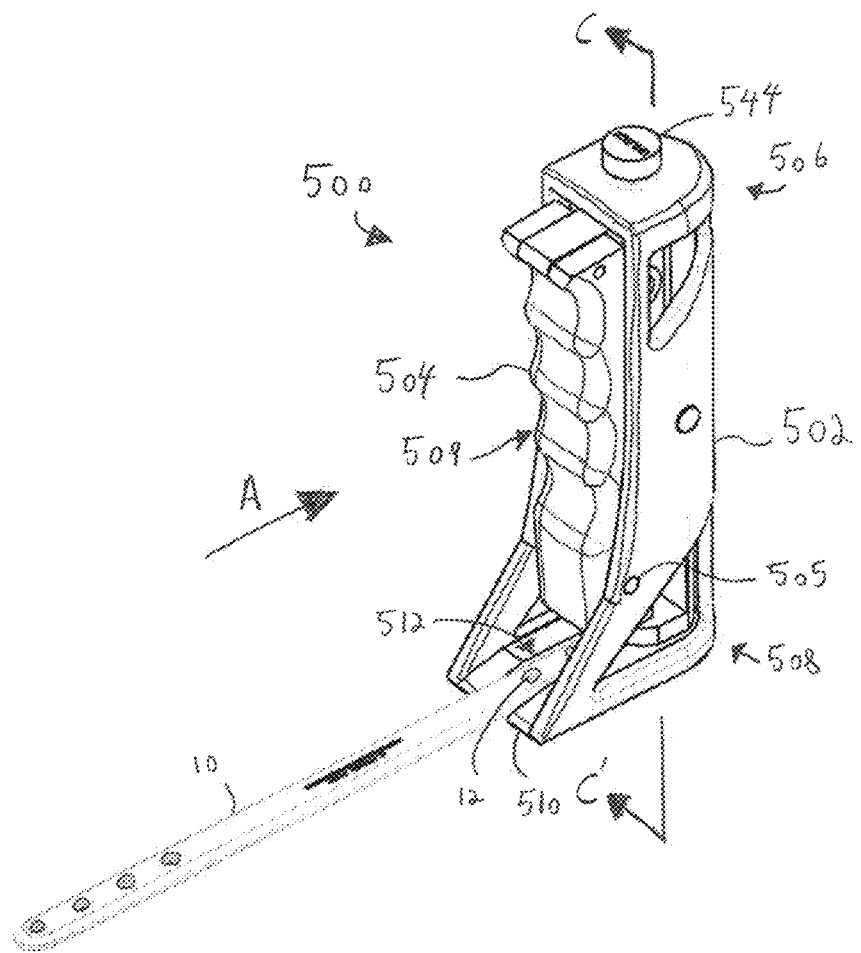
Figure 5B:
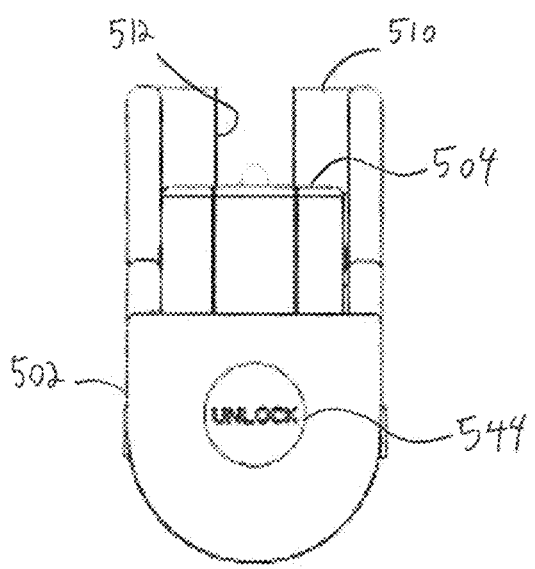
Figure 5I:
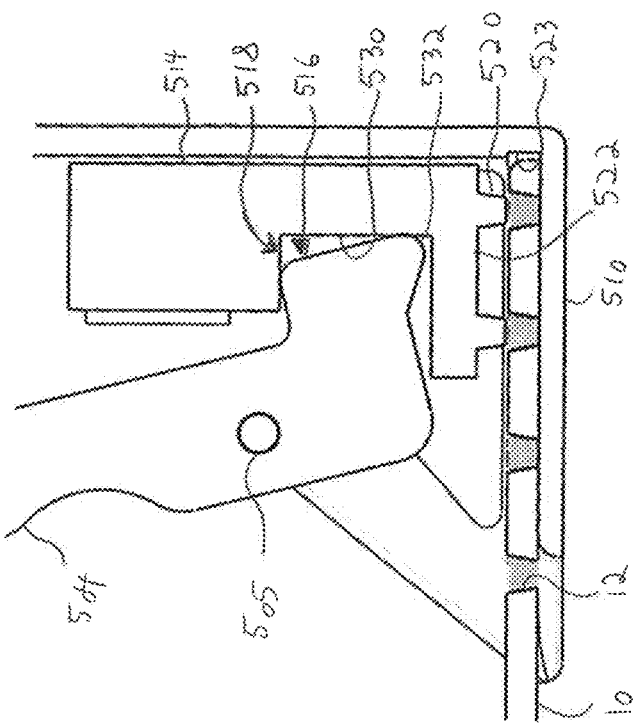
Figure 5H:
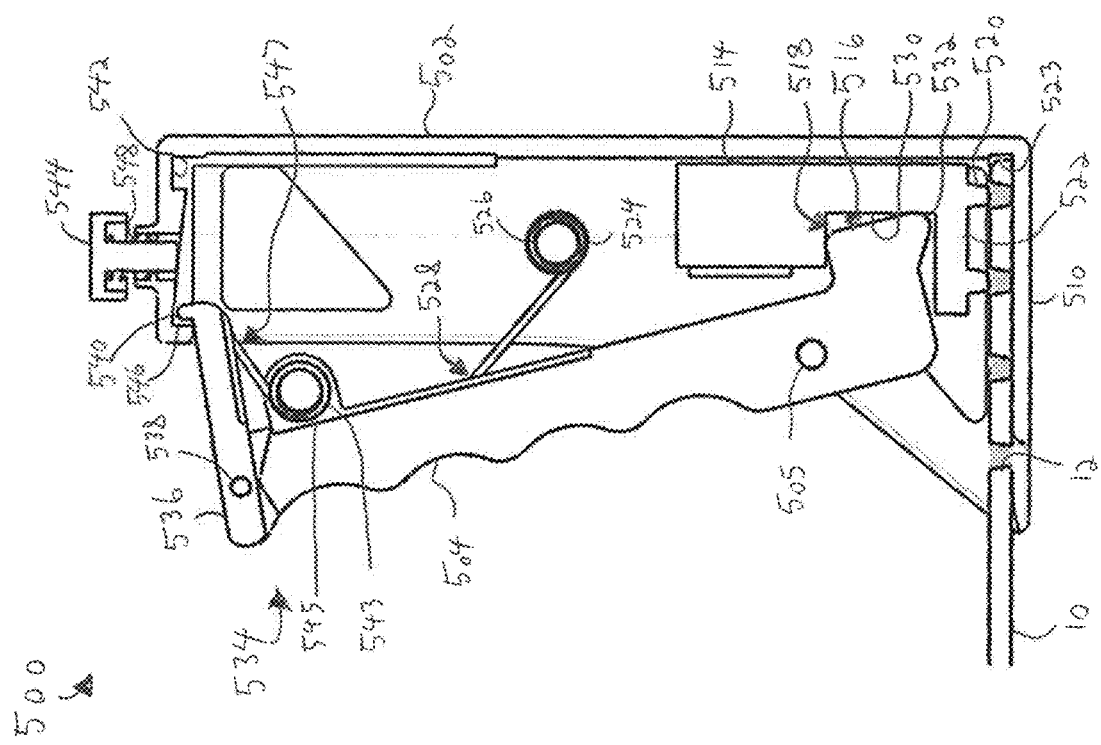

In some embodiments, the plate locking mechanism 410 further includes a plate engagement body 424 disposed beneath the actuator body 416. The plate engagement body 424 is coupled to the actuator body 416 in a way that allows the actuator body 416 to rotate relative to the plate engagement body. For example, as shown in FIG. 4D, the plate engagement body 424 may include a spherical protrusion 426 extending upwardly from an upper surface 428 of the plate engagement body 424 into a corresponding spherical recess 430 formed in a bottom surface 432 of the actuator body 416. Such a coupling enables the two bodies 416, 424 to be coupled, while allowing for the rotation of the actuator body 416 relative to the plate engagement body 424.

The plate engagement body 424 includes one or more engagement members 434 (two shown in FIG. 4D) extending downwardly from a bottom surface 436 of the plate engagement body 424. The engagement members 434 are configured to engage (i.e., be inserted into) the holes 12 of the plate 10. After the plate 10 is inserted into the opening 407, the holes 12 are disposed beneath the one or more engagement members 434. Rotation of the lever 414 in the first direction causes the actuator body 416 and the plate engagement body 424 downwards so that the one or more engagement members 434 are inserted into corresponding holes 12. The user may subsequently insert the plate 10 into patient and manipulate the plate as desired. When the user wishes to disengage the plate inserter 400 from the plate 10, the user rotates the lever 414 in the second direction so that the engagement members 434 retract upwards and out of engagement with the holes 12.

FIGS. 5A-5I depict a plate inserter 500 in accordance with embodiments of the present disclosure. In some embodiments, the plate inserter 500 includes a frame 502 and an actuator handle 504 rotatably coupled to the frame 502 via a pin connection 505. The frame 502 extends from an upper end 506 to a lower end 508. As shown more clearly in FIGS. 5A, 5C, and 5D, the lower end 508 includes a plate support base 510 having a groove 512 configured and dimensioned to receive the plate 10 therein. The actuator handle 504 also includes a gripping portion 509 configured to easily be gripped by a user's hand.

As shown more clearly in FIGS. 5C-5D and 5H-5I, the plate inserter 500 further includes an engagement body 514 disposed within the frame 502. A lower portion 516 of the actuator handle 504 extends into an opening 518 of the engagement body 514 to cause vertical movement of the engagement body 514, as will be described below. The engagement body 514 includes at least one engagement member 520 (two shown) extending downwardly from a bottom surface 522 of the engagement body 514. The engagement members 520 are configured to engage (i.e., be inserted into) the holes 12 of the plate 10. In use, the plate 10 is inserted into the groove 512 until it contacts a back wall 523 of the frame 502. Subsequently, the engagement members 520 are inserted into the holes 12 as described below.

In some embodiments, the plate inserter 500 includes a first torsion spring 524 mounted on a post 526 within the frame 502. A free end 528 of the torsion spring 524 is in contact with the actuator handle 504 to bias it towards the position shown in FIGS. 5H and 5I, in which the engagement members 520 do not engage the holes 12 of the plate 10. To move the engagement members 520 into the holes 12, thus fixing the plate 10 to the inserter 500, the user grips the gripping portion 509 and squeezes the actuator handle 504 in the direction indicated by arrow A (shown in FIGS. 5A and 5C). When this movement occurs, the actuator handle 504 rotates in a clockwise direction about the pin connection 505, thus moving the lower portion 516 away from a back wall 530 of the opening 518. The lower portion 516 includes a tip 532 that is shaped so that movement of the lower portion 516 away from the back wall 530 results in the tip 532 exerting a downward force on the engagement body 514, thus moving the engagement members 520 into the holes 10.

Referring to FIGS. 5E-5G, to retain the inserter 500 in the plate engagement position just described, an upper portion 534 of the actuator handle 504 includes a retention member 536 pivotally coupled to the upper portion 534 via a pin connection 538. The retention member 536 includes an upwardly extending lip 540 configured to be disposed in a corresponding retention recess 542 formed on the interior of the frame 502 when the inserter 500 is in the plate engagement position (shown in FIGS. 5C-5E). A second torsion spring 543 is coupled to the actuator handle 504 via a pin connection 545. A free end 547 of the torsion spring 543 contacts the retention member 536 and is configured to bias the retention member 536 upward. When the lip 540 of the retention member 542 is disposed within the retention recess 542 under the bias of the second torsion spring 536 (as shown in FIG. 5E), the inserter 500 is locked in the plate engagement position so that the plate 10 can be manipulated as desired.

To disengage the engagement members 520 from the holes 12, a button 544 disposed in the upper end 506 is pressed. Pressing the button 544 causes a lower portion of the button 544 to push down on the retention member 536 (as shown in FIG. 5F) to overcome the biasing force of the second torsion spring 543, thus moving the lip 540 out of the retention recess 542 (as shown in FIG. 5G). Under the biasing force of the first torsion spring 524, the actuator handle 504 returns to the disengaged position shown in FIG. 5H. In some embodiments, the frame 502 includes a lip 546 that retains the upwardly extending lip 540 when the actuator handle returns to the disengaged position (as shown in FIG. 5G). In some embodiments, a biasing element 548 (e.g., a helical spring) may be disposed between the button 544 and the frame 502 to bias the button 544 upwards such that the button 544 returns to its original position after it is pressed down to release the retention member 536.

Figure 6B:
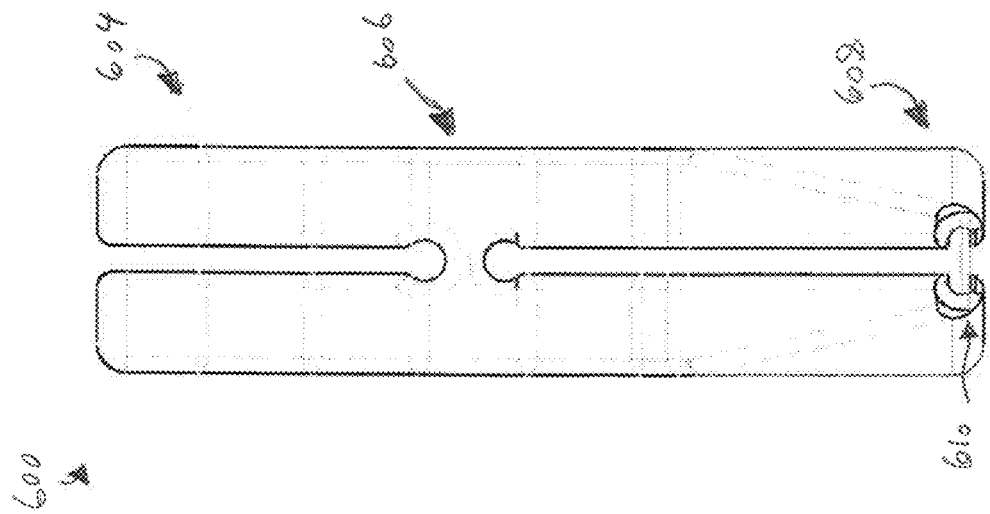
FIGS. 6A and 6B depict an apparatus for inserting a plate in accordance with embodiments of the present disclosure.
Figure 6A:
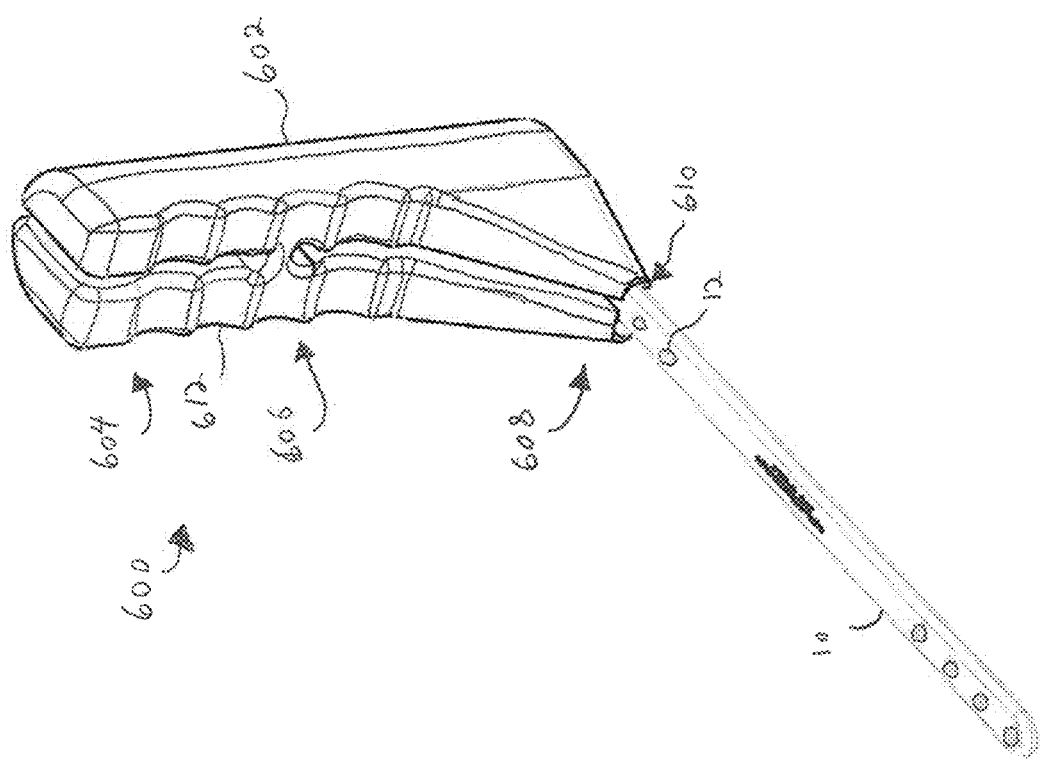

FIGS. 6A and 6B depict a plate inserter 600 in accordance with embodiments of the present disclosure. In some embodiments, the plate inserter 600 includes a body 602 having an upper portion 604, an intermediate portion 606, and a lower portion 608. The upper and lower portions of the body 604, 608 are separated into two independent halves. The intermediate portion 606 joins the two halves of the body 602. The lower portion 608 includes an opening 610 configured to receive the plate 10 therein. In some embodiments, the size of the opening 610 is slightly smaller than the plate 10 such that insertion of the plate 10 into the opening 610 causes outward flexure of the lower portion 608 of the body 602. As a result, the plate 10 is held within the opening 10 by compression caused by the flexure of the body 602. As shown in FIGS. 6A and 6B, the upper portion 604 and at least a portion of the lower portion 608 include a gripping surface 612 configured to be grasped by the hand of a user. In use, the plate 10 is inserted into the opening 610 until it contacts an interior rear surface (not shown) of the body 602. As noted above, the plate 10 is held within the opening 610 by compression of the lower portion 608. A user may then manipulate the plate 10 disposed within the inserter 600 as desired. When it is time for the plate 10 to be removed from the inserter 600, the user squeezes the upper portion 604 inwards, causing the lower portion 608 to flex outward, thus loosening the plate and allowing for its removal.

Figure 7B:
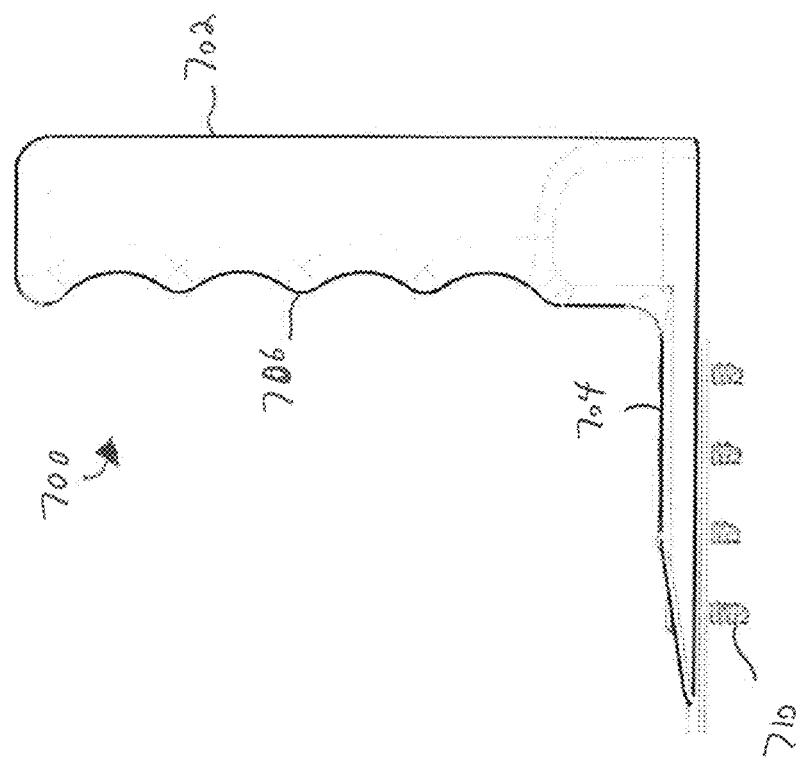
FIGS. 7A and 7B depict an apparatus for inserting a plate in accordance with embodiments of the present disclosure.
Figure 7A:
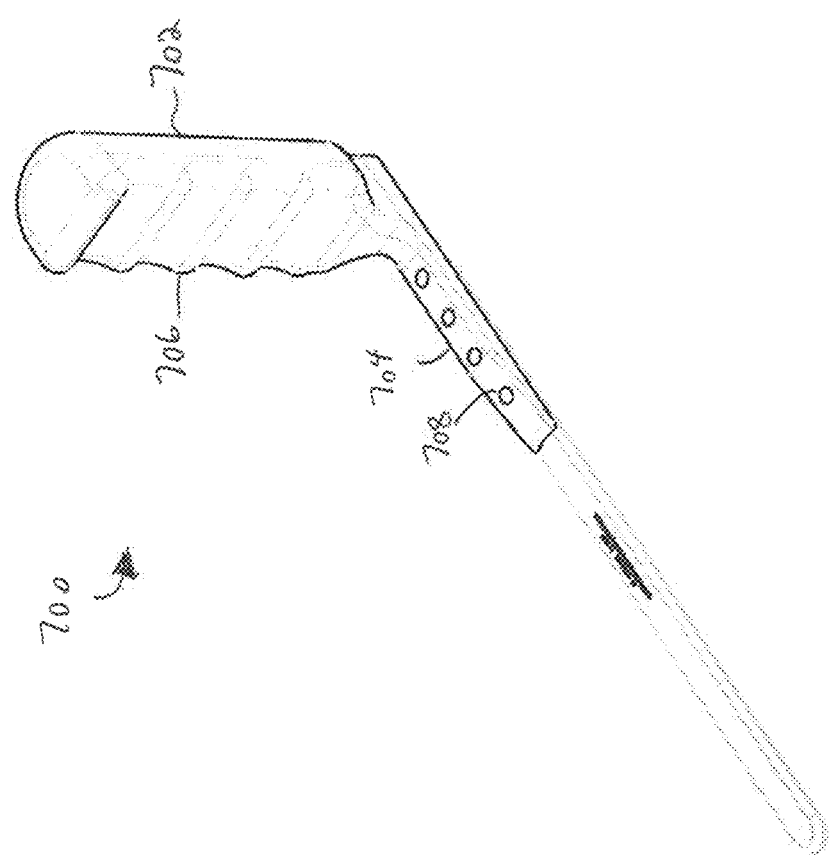

FIGS. 7A and 7B depict a plate inserter 700 in accordance with embodiments of the present disclosure. In some embodiments, the plate inserter 700 includes a body 702 coupled to an engagement portion 704. Together, the body 702 and the engagement portion 704 form an L-shape. In some embodiments, the body 702 and the engagement portion 704 are integrally formed (i.e., monolithic). The body 702 includes a gripping surface 706 configured to be gripped by a user's hand. In some embodiments, the engagement portion 704 includes at least one engagement hole 708 (four shown in FIGS. 7A and 7B) that correspond to at least one of the holes 12 of the plate 10. The engagement holes 708 are configured to receive corresponding fasteners 710 (e.g., screws) such that the fasteners 710 extend through the engagement holes 708 and corresponding holes 12 to couple the plate 10 to the engagement portion 704. The inserter 700 advantageously provides users the ability to use some engagement holes 708 for coupling the plate 10 to the inserter 700 and the remaining engagement holes 708 for securing the plate 10 directly to bone while the plate 10 is still attached to the inserter 700. After the plate 10 has been moved/manipulated as desired, the user removes the fasteners 710 to decouple the plate 10 from the inserter 700.

FIGS. 8A-8E depict a plate inserter 800 in accordance with embodiments of the present disclosure. The plate inserter 800 includes some elements similar to the inserter 400 described above. For example, the inserter 800 includes a body 802 extending from an upper end 804 to a lower end 806, a gripping portion 808, a plate locking mechanism 810 having an actuator 812 that extends through the upper end 804. Also similar to the inserter 400, the actuator 812 includes a rotatable lever 814 coupled to an actuator body 816. The actuator body 816 includes a protruding element 818 that extends radially outward from the actuator body 816 into a groove 820 formed on an interior wall 822 of the body 802. The groove 820 is sloped such that when a user turns the lever 814 (and thus the actuator body 816) in a first direction, movement of the protruding element 818 along the groove 820 forces the actuator body 816 to move downwards. Turning the lever 814 in a second direction opposite the first direction forces the actuator body 816 to move upwards.

However, the inserter 800 differs from the inserter 400 in that the body 802 includes a horizontal portion 813 extending from the lower end 806 of the body. In some embodiment, the horizontal portion 813 includes one or more collets 815 (two shown in FIGS. 8B-8E) configured to be inserted into the holes 12 of the plate 10. Each collet 815 includes a conical portion 817 extending downwards from the horizontal portion 813 and terminating at a collar 819. Each collet 815 also includes two or more slots 821 (one shown in FIGS. 8B-8E due to cross-sectional view) separating the collet 815 into two or more prongs 823. The collets 815 have a maximum diameter that is less than the diameter of the holes 12 so that the collets 815 can be inserted into the holes 12 with relative ease.

Figure 8A:
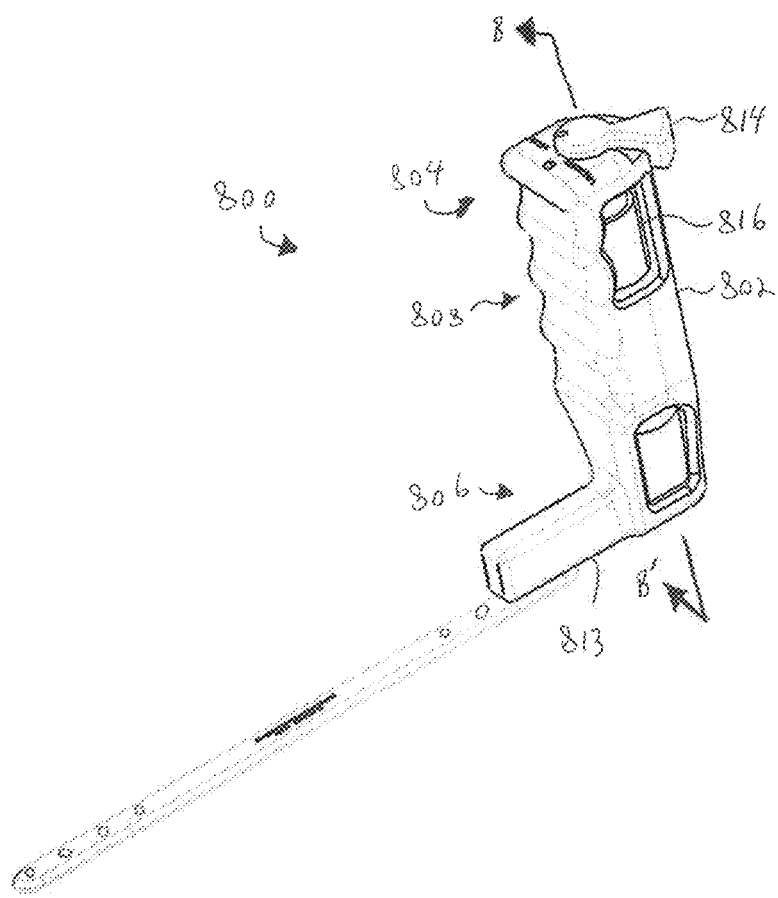
FIGS. 8A-8E depict an apparatus for inserting a plate in accordance with embodiments of the present disclosure.
Figure 8B:
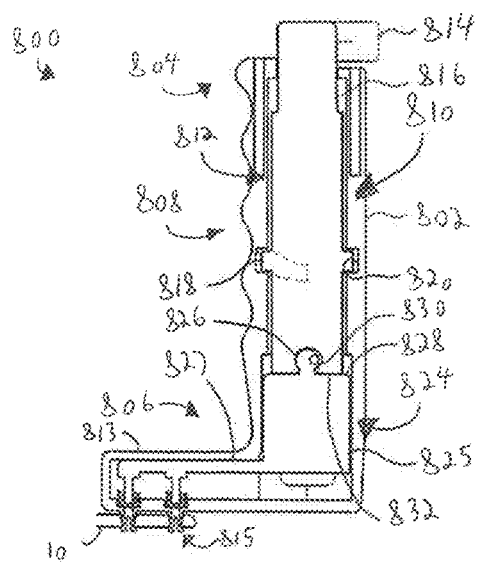
Figure 8C:
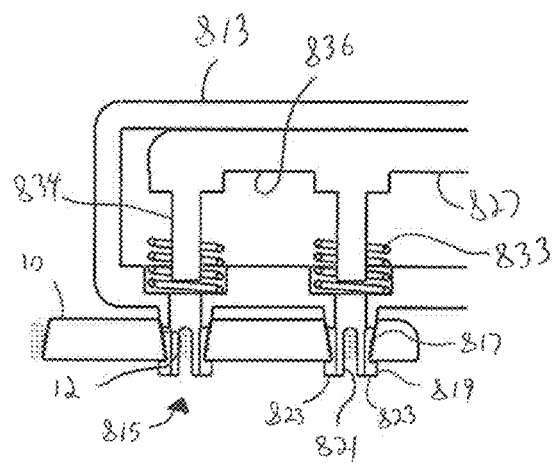
Figure 8D:
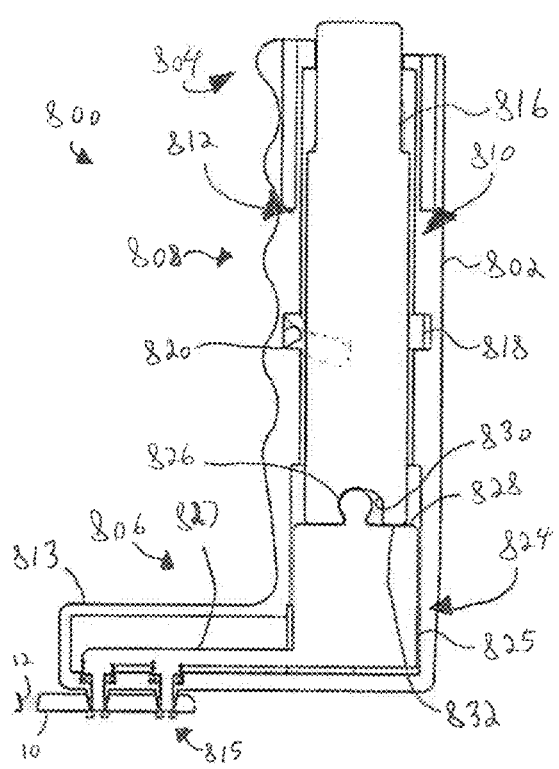
Figure 8E:
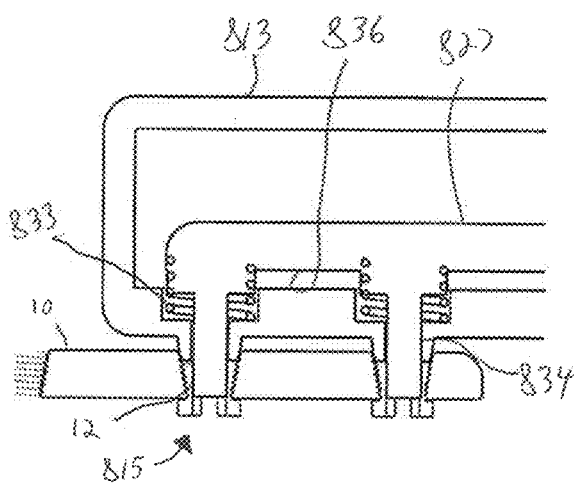

The plate locking mechanism 810 further includes a plate engagement body 824 disposed beneath the actuator body 816. The plate engagement body 824 includes a main body 825 and a horizontal arm 827 extending from the main body 825 into the horizontal portion 813 of the body 802. Similar to the plate engagement body 424, the plate engagement body 824 is coupled to the actuator body 816 in a way that allows the actuator body 816 to rotate relative to the plate engagement body. For example, as shown in FIGS. 8B and 8D, the plate engagement body 824 may include a spherical protrusion 826 extending upwardly from an upper surface 828 of the plate engagement body 824 into a corresponding spherical recess 830 formed in a bottom surface 832 of the actuator body 816. Such a coupling enables the two bodies 816, 824 to be coupled, while allowing for the rotation of the actuator body 816 relative to the plate engagement body 824.

The plate engagement body 824 includes one or more posts 834 (two shown in FIGS. 8B-8E) corresponding to the one of more collets 815. The one or more posts 834 extend downwardly from a bottom surface 836 of the horizontal arm 827 and are configured to engage (i.e., be inserted into) the collets 815. After collets 815 are inserted into the holes 12, the one or more posts 834 are inserted through central openings 829 of the collets 815 to deflect the prongs 823 radially outward. As a result, the plate 10 is locked onto the inserter 800. The collars 819 of the collets 815 provide a retention force so that the plate 10 does not slide off after the expansion of the collets 815.

In use, the inserter 800 is provisionally coupled to the plate 10 by insertion of the collets 815 through the holes 12. Subsequently, the lever 814 is rotated in the first direction to force the actuator body 816 and the plate engagement body 824 downwards so that the posts 834 move into the collets 815, thus forcing the prongs radially outward and locking the plate 10 to the inserter 800. The user may subsequently insert the plate 10 into patient and manipulate the plate 10 as desired. When the user wishes to disengage the plate inserter 800 from the plate 10, the user rotates the lever 814 in the second direction so that the posts 834 retract upwards and out of the collets 815. In some embodiments, one or more springs 833 may be disposed about corresponding ones of the one or more posts 834 to bias the engagement body 824 towards the unlocked position, thus ensuring the posts 834 do not unintentionally drop into the collets 815.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An apparatus for inserting a bone plate to a target site, the apparatus comprising:
   a body extending from an upper end to a lower end;
   a plate receiving portion configured to receive the bone plate; and
   a plate engaging mechanism configured to couple the bone plate to the body,
   wherein the body includes a gripping surface configured to be gripped by a user's hand,
   wherein the plate receiving portion is an opening formed proximate the lower end of the body,
   wherein the plate engaging mechanism comprises:
   an actuator; and
      a plate engagement body configured to lock the bone plate to the apparatus, the plate engagement body having one or more plate engagement members extending downwardly from the plate engagement body and configured to be inserted into holes of the bone plate,
   wherein the actuator extends through the upper end of the body and includes a rotatable lever coupled to an actuator body disposed within the body of the apparatus, wherein the actuator body includes a protruding element extending radially outwards from the actuator body, wherein a groove is formed in an inner wall of the body of the apparatus to receive the protruding element therein, and wherein the groove includes a slope such that rotation of the lever in a first direction forces the actuator body downwards from an initial position and rotation of the lever in a second direction forces the actuator upwards from an engaged position.

2. The apparatus of claim 1, wherein the plate engagement body includes a spherical protrusion extending upwardly from an upper surface of the plate engagement body, wherein the actuator body includes a corresponding spherical recess formed in a bottom surface of the actuator body and configured to receive the spherical protrusion of the plate engagement body such that rotation of the actuator body relative to the plate engagement body is allowed and such that downward or upward motion of the actuator body results in corresponding downward or upward motion of the plate engagement body.

3. The apparatus of claim 1, wherein the body of the apparatus includes an upper portion, an intermediate portion, and a lower portion, wherein the upper and lower portions are separated into two independent halves, wherein the intermediate portion joins the two independent halves of the upper and lower portions, wherein a size of the opening is smaller than a size of the bone plate such that when the bone plate is inserted into the opening, the bone plate causes outward flexure of the lower portion, and wherein squeezing of the upper portion causes outward flexure of the lower portion.

4. The apparatus of claim 1, wherein the body includes a frame, and wherein the place receiving portion opening is formed in a groove formed in a lower portion of the frame.

5. The apparatus of claim 1, wherein the plate receiving portion extends horizontally outward from a bottom portion of the body and is configured to abut the bone plate.

* * * * *